(12) United States Patent
Humayun et al.

(10) Patent No.: US 7,794,437 B2
(45) Date of Patent: Sep. 14, 2010

(54) RESERVOIRS WITH SUBRETINAL CANNULA FOR SUBRETINAL DRUG DELIVERY

(75) Inventors: Mark Humayun, Glendale, CA (US); Eugene De Juan, La Canada Flintridge, CA (US)

(73) Assignee: Doheny Retina Institute, Los Angeles, CA (US)

( * ) Notice: Subject to any disclaimer, the term of this patent is extended or adjusted under 35 U.S.C. 154(b) by 569 days.

(21) Appl. No.: 10/543,083

(22) PCT Filed: Jan. 26, 2004

(86) PCT No.: PCT/US2004/002214
§ 371 (c)(1),
(2), (4) Date: Jan. 4, 2006

(87) PCT Pub. No.: WO2004/066871
PCT Pub. Date: Aug. 12, 2004

(65) Prior Publication Data
US 2006/0200097 A1    Sep. 7, 2006

Related U.S. Application Data

(60) Provisional application No. 60/442,323, filed on Jan. 24, 2003.

(51) Int. Cl.
*A61M 35/00* (2006.01)
(52) U.S. Cl. .................................................. 604/300
(58) Field of Classification Search .................. 604/289, 604/294, 295, 297, 298, 300
See application file for complete search history.

(56) References Cited

U.S. PATENT DOCUMENTS

| | | | |
|---|---|---|---|
| 4,781,675 A | | 11/1988 | White |
| 5,178,604 A | | 1/1993 | Baerveldt et al. |
| 5,370,607 A | * | 12/1994 | Memmen ...................... 604/8 |
| 5,454,796 A | * | 10/1995 | Krupin ...................... 604/294 |
| 5,725,493 A | * | 3/1998 | Avery et al. ................... 604/9 |
| 5,830,173 A | | 11/1998 | Avery et al. |

\* cited by examiner

*Primary Examiner*—Manuel A Mendez
(74) *Attorney, Agent, or Firm*—Edwards Angell Palmer & Dodge LLP; Peter F. Corless; Lisa Swiszcz Hazzard (57) ABSTRACT

Featured are devices and methods for administering a therapeutic medium to the posterior segment of an eye including instilling or disposing the therapeutic medium sub-retinally. Such instillation is accomplished by providing a reservoir containing a therapeutic medium to which is fluidly coupled a cannula and inserting a portion of the cannula sub-retinally, whereby the therapeutic medium within the reservoir is coupled to and dispersed subretinally via the cannula.

27 Claims, 5 Drawing Sheets

RESERVOIRS WITH SUBRETINAL CANNULA FOR SUBRETINAL DRUG DELIVERY

This application claims the benefit of U.S. Provisional Application Ser. No. 60/442,323 filed Jan. 24, 2003, the teachings of which are incorporated herein by reference.

FIELD OF INVENTION

The present invention relates to devices and methods for treating eyes, such as eyes of mammals having eye disorders or diseases, more particularly to devices and methods for administering a therapeutic medium or agent sub-retinally, yet more particularly to devices and methods for administering such therapeutics or agents to the tissues of the eye so that the pharamacodynamic action of the such therapeutics/agents is localized at the choroid and the retina and more specifically to devices and methods for administering such therapeutics/agents using a device including a sub-retinal cannula through which such therapeutics/agents are administered subretinally.

BACKGROUND OF THE INVENTION

There are a number of vision-threatening disorders or diseases of the eye of a mammal including, but not limited to diseases of the retina, retinal pigment epithelium (RPE) and choroid. Such vision threatening diseases include, for example, ocular neovascularization, ocular inflammation and retinal degenerations. Specific examples of these disease states include diabetic retinopathy, chronic glaucoma, retinal detachment, sickle cell retinopathy, age-related macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases, retinal ischemia, choroidal vascular insufficiency, choroidal thrombosis, neovascularization of the optic nerve, diabetic macular edema, cystoid macular edema, macular edema, retinitis-pigmentosa, retinal vein occlusion, proliferative vitreoretinopathy, angioid streak, and retinal artery occlusion, and, neovascularization due to penetration of the eye or ocular injury.

For example, age-related macular degeneration (AMD) is the leading cause of irreversible severe central vision loss in Caucasians fifty years old and older in the United States. According to the 1990 U.S. census, approximately 750,000 people over 65 years of age were estimated as severe visual impairment in one or both eyes from AMD. Also, the number of cases of AMD has been predicted to increase from 2.7 million in 1970 to 7.5 million by the year 2030.

Roughly 80 percent of the AMD cases involve non-neovascular conditions, for which there are no effective treatments. For the remaining cases involving neovascularization, currently available treatments are sub-optimal. Perhaps the best known therapy is photodynamic therapy (PDT), however, while this therapy has received significant intention in both the ophthalmic and financial investment communities, it is useful in only about 20 percent of neovascular AMD cases. In addition, this particular therapy is not a simple or inexpensive treatment. The procedure generally needs to be repeated every three months for at least two years, with approximate total cost of $12,250.

A number of angiostatic agents are currently under investigation for the treatment of AND. Thalidomide, for example, is known to be a powerful angiostatic agent. It systemic side effects, however, include peripheral neuropathy, central nervous system depression, and embryptoxicity. In addition, these systemic side effects have limited the dosage administered to patients for the treatment of sub-retinal neovascularization. Systemic inhibition of angiogenesis in older patients can also interfere with the development of collateral circulation, which has a role in the prevention of central nervous system as well as cardiac ischemic events.

A number of techniques or methodologies have been developed to deliver drugs to the various tissues or structure that make up the mammalian eye as described hereinafter to treat a wide range of disorders or diseases of the eye. However, delivery of drugs, proteins and the like to the eye(s) of mammals so as to achieve the desired therapeutic or medical effect, especially to the retina and/or the choroids, has proven to be challenging, most of which is owed to the geometry, delicacy and/or behavior of the eye and its components. A brief description of various conventional methods or techniques for delivering drugs to the tissues of the eye and the shortcomings thereof are hereinafter described.

Oral ingestion of a drug or injection of a drug at a site other than the eye can provide a drug systemically, however, such a systemic administration does not provide effective levels of the drug specifically to the eye. In many ophthalmic disorders involving the retina, posterior tract, and optic nerve, adequate levels of the drug cannot be achieved or maintained by oral or parenteral routes of administration. Thus, further and repeated administration of the drug would be necessary to achieve the desired or adequate levels of concentration of the drug. Such further and repeated administrations of such drugs, however, may produce undesired systemic toxicity.

Ophthalmic conditions have also been treated using drugs applied directly to the eye in either liquid or ointment form. This route of administration (i.e., topical administration), however, is only effective in treating problems involving the superficial surface of the eye and diseases that involve the cornea and anterior segment of the eye, such as for example, conjunctivitis. Topical administration of drugs is ineffective in achieving adequate concentrations of a drug(s) in the sclera, vitreous, or posterior segment of the eye. In addition, topical eye drops may drain from the eye through the nasolacrimal duct and into the systemic circulation, further diluting the medication and risking unwanted systemic side effects. Furthermore, delivery of drugs in the form of topical eye drops is also of little utility because the drug cannot cross the cornea and be made available to the vitreous, retina, or other subretinal structures such as the retinal pigment epithelium ("RPE") or choroidal vasculature and/or is highly unstable and therefore not easily formulated for topical delivery. Moreover, data also indicates that it is not unusual for up to 85% of topically applied agents to be removed by the eye's blink mechanism/reflex.

Direct delivery of drugs to the eye by a topical insert has also been attempted, however, this method is not desirable. Such topical inserts require patient self-administration and thus education on their insertion into and removal from the eye. Consequently, this technique demands a certain degree of manual dexterity that can be problematic for geriatric patients who are particularly susceptible to certain eye disorders that appear age related (e.g., age related macular degeneration). Also, in many instances such topical inserts may cause eye irritation and such inserts are prone to inadvertent loss due to eyelid laxity. In addition, these devices provide a source of drug only to the cornea and anterior chamber, and thus do not provide any pharmacologic advantage over topical eye drops or ointments. Thus, such devices have limited, if any at all, utility for providing an effective source of drugs to the vitreous or tissues located in the posterior segment of the eye.

As a consequence most methods for treating eye disorders or diseases in the posterior segment, or the back-of-the-eye, involve intravitreal delivery of the drug. One such technique for intravitreal delivery is accomplished by intraocular injection of the drug or microspheres containing the drug directly into the vitreous or by locating a device or capsule containing the drug in the vitreous, such as that described in U.S. Pat. No. 5,770,589. Intravitreal injection of a drug is-an effective means of delivering the drug to the posterior segment of the eye in high concentrations, but it is not without its shortcomings. It is well known that drugs that are initially located within the vitreous are removed from the vitreous over time via the anterior segment of the eye. If the ocular condition is anything other than acute, this technique necessarily requires follow-up injections in order to maintain an adequate therapeutic concentration within the vitreous. This, in turn, presents problems because each additional intraocular injection carries with it a realistic risk of infection, hemorrhage and/or retinal detachment.

In addition, it also is well known that many therapeutic drugs cannot easily diffuse across the retina. Thus, the dose being administered and maintained in the vitreous has to take into account the amount that can diffuse across the retinal boundary as well as how long the drug is retained in effective amounts within the vitreous. For example, it has been observed from animal studies that 72 hours after injection of triamcinolone, less than 1% of the triamcinolone present in the vitreous was associated with other tissues including the retina, pigment epithelium, and sclera. In addition to the relative effectiveness of drug delivery across the barrier, complications or side effects have been observed when using the direct injection into vitreous technique with some therapeutics.

For example, compounds classified as corticosteroids, such as triamcinolone, can effectively treat some forms of neovascularization such as corneal neovasularization. When these compounds were used to treat neovscularization of the posterior segment by direct injection, these compounds were observed to cause undesirable side effects in many patients. The adverse affects or undesirable side effects being observed included elevations in intraocular pressure and the formation of, or acceleration of, the development of cataracts. Elevations in intraocular pressure are of particular concern in patients who are already suffering from elevated intraocular pressure, such as glaucoma patients. Moreover, a risk exists that the use of corticosteroids in patients with normal intraocular pressure will cause elevations in pressure that result in damage to ocular tissue. Since therapy with corticosteroids is frequently long term, i.e., several days or more, a potential exists for significant damage to ocular tissue as a result of prolonged elevations in intraocular pressure attributable to that therapy.

Consequently, efforts in the area of intravitreal delivery also have included delivery by locating a sustained release implant, capsule or other such device or mechanism that is in communication with: the vitreous and which is configured so as to provide a release over time into the vitreous of the contained drug. Examples of such controlled release devices are described in U.S. Pat. Nos. 6,217,895; 5,773,019; 5,378,475 and US Patent Application Publication No. 2002/0061327.

A common feature of the techniques/instruments described therein, is that a surgical incision is required to be made at the outset of a procedure so that the implant, capsule or other such device can be inserted through the eye and located in the vitreous. These methods and techniques also necessarily involve the use of sutures following completion of the procedure to seal or close the incision so as to prevent loss of vitreous material. As is known to those skilled in the art, maintaining the volume of the posterior segment or vitreous is necessary to maintaining the shape and optical arrangement of the eye. Such a course of treatment also increases the duration and cost as well as the realistic risks of corneal ulceration, cataract formation, intraocular infection, and/or vitreous loss that accompany these procedures.

There is described in U.S. Pat. Nos. 5,273,530 and 5,409,457 an instrument and methodology to transplant donor cells, more specifically donor retina cells, in the sub-retinal space. It also is described therein that the instrument also can be used to inject or remove material from the vitreous. According to the described methodology, the instrument is shaped and dimensioned so it can be inserted into an eye orbit along an insertion path that extends along the periphery of the eye and so as to place the tip adjacent to the retina or sub-retinal region. The tip is then moved generally in the medial direction so the tip pierces the exterior of the eye and so the tip resides in the sub-retinal region or in the vitreous depending upon how much the tip is moved. In order to prevent over-insertion of the tip, a collar is provided about the tip so as to limit the distance the tip can be inserted into the eye.

There also is described in US Patent Application Publication 2002/0055724, an instrument for sub-retinal transplantation of retinal cells, epithelium and choroid within their normal planar configuration as a graft into the sub-retinal region of an eye. The described, instrument is inserted into an opening in the eye using either a transcorneal surgical approach or a trans-choroidal and scleral surgical approach. According to this technique the instrument is advanced under the retina to detach the retina so that the graft can be inserted. As noted in U.S. Pat. No. 5,273,530, the penetration of the anterior part or segment of the eye, using the transcorneal or the transscleral route creates the risks of corneal ulceration, cataract formation and other anterior penetration problems. Also using either approach, a surgical incision is created at the outset of a procedure so that the instrument can be inserted and sutures are used following completion of the procedure to seal or close the incision so as to prevent loss of vitreous material (i.e., aqueous humor).

It thus would be desirable to provide, a new device and methods for treating an eye, particularly treating retinal and/or choridal disorders or diseases, whereby a depot of a therapeutic medium, compound or agent such as a corticosteriod, can be controllable and continuously instilled in the sub-retinal space of the eye. It would be particularly desirable to provide such a method that would localize the action of the therapeutic medium, compound or agent at the retina and the choroidea while minimizing such action in other tissues of the, eye. It also would be desirable to provide such a device that would controllably release the therapeutic medium, compound or agent subretinally and be simple in construction.

SUMMARY OF THE INVENTION

The present invention features devices and methods for administering or delivering a therapeutic medium to a posterior segment of a mammalian eye, more particularly a human eye, where such a therapeutic medium includes, but is not limited to drugs, medicaments, antibiotics, antibacterials, antiproliferatives, neuroprotectives, anti-inflammatories (steroidal and non-sterodial), growth factors, neurotropic factors, antiangiogenics, thromobolytics or genes. The present invention also features methods for the treatment and prevention of disorders and or diseases of the eye, in particular retinal/choroidal disorders or diseases, through sub-retinal administration or sub-retinal prophylatic administration of such a therapeutic medium. More particularly, such devices and methods according to the present invention include instilling or disposing a therapeutic amount of a therapeutic medium sub-retinally or into the sub-retinal space, more specifically so as to localize the action of the therapeutic medium at the choroid and the retina of the eye. In a more particular embodiment, the device includes a compartment in which is stored the therapeutic medium, which compartment is fluidly coupled to a cannula and said instilling or disposing includes localizing a portion of the cannula subretinally, whereby the therapeutic medium is dispersed subretinally from the cannula portion so as to be instilled sub-retinally or dispersed in the sub-retinal space.

Such methods bypass the mechanisms that limit effective delivery of therapeutic media to the retina/choriod when they are injected directly into the vitreous, thereby permitting more sustained therapy for the target tissue. Moreover, locating such a therapeutic medium sub-retinally or in the sub-retinal space also reduces the side effects typically associated with the injection of drugs into the vitreous.

Exemplary therapeutic mediums include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouiracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Antiproliferatives include any of a number of compounds, agents, therapeutic mediums or drugs known to those skilled in the art that inhibit the proliferation of cells. Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized as having the property of counteracting or suppressing the inflammatory process. Non-steroidal inflammatory drugs or compounds comprise a class of drugs which shares the property of being analgesic, antipyretic and anti-inflammatory by way of interfering with the synthesis of prostaglandins. Such non-steroidal anti-inflammatories include, but are-not limited to, indomethacin, ibuprofen, naxopren, piroxicam and nabumetone.

Such anti-inflammatory steroids contemplated for use in the methodology of the present invention, include those illustrated in FIGS. 6A-C and also that described in U.S. Pat. No. 5,770,589, the teachings of which are incorporated herein by reference. In an exemplary embodiment, an anti-inflammatory steroid contemplated for use in the methodology of the present invention is triamcinolone acetonide (generic name). Corticosteroids contemplated for use in the methodology of the present invention include, for example, triamcinolone, dexamethasone, fluocinolone, cortisone, prednisolone, flumetholone, and derivatives thereof (See also U.S. Pat. No. 5,770,589, the teachings of which are incorporated herein by reference).

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation. In the present invention, such growth factors include, but are not limited to, pigment epithelium derived factor and basic fibroblast growth factor.

As is known to those skilled in the art, neurotropic factors is a general term used to describe growth factors and cytokines that can enhance neuronal survival and axonal growth and that regulate synaptic development and plasticity in the nervous system. In the present invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries. Such compounds, agents, therapeutic mediums or drugs include, but are not limited to, anecortave acetate and anti VEGF antibody.

Thrombolytics, as is known to those skilled in the art include any of a number of compounds, agents, therapeutic mediums or drugs that dissolve blot clots, or dissolve or split up a thrombus. Such thrombolytics include, but are not limited to, streptokinase, tissue plasminogen activator or TPA and urokinase.

In another aspect of the present invention there is featured a therapeutic medium delivery device that is configured and arranged (i.e., designed) so as to include a compartment or reservoir and a cannula member that is fluidly coupled to the interior volume of the reservoir. The compartment or reservoir is configured and arranged so as to contain an amount of the therapeutic medium to be instilled subretinally. In further embodiments, the therapeutic medium delivery device is further configured and arranged so as to be capable of be localized within the body in an external, pars plana, intraocular lens and epiretinal presentation.

The cannula is thin member, having a length sufficient to traverse between the treatment site and the location of the reservoir that can be remote from the treatment site. The cannula, more particularly at least the portion of the cannula to be localized sub-retinally, is sized so as to be capable of being inserted through the retina to the subretinal space as well as to remain subretinally following such insertion during normal physiological action of the eye.

The portion of the cannula localized subretinally also is preferably configured and arranged so as to control the release of the therapeutic medium sub-retinally. In more particular embodiments, this portion of the cannula is configured and arranged so that the therapeutic medium drug is controllably dispensed from the cannula and released into the subretinal space, physiologically via the retinal pigment epithelium pump.

In a more specific embodiment, the size of the reservoir is modified in accordance with the therapeutic medium to drug administered and/or the indication. In illustrative embodiments, the cannula and reservoir are arranged so the cannula emerges from the reservoir, for example, from underneath or the side of the reservoir.

In further embodiments, the reservoir is made from a material, such as a polymer, that can withstand repeated piercing by a needle without causing leakage. In this way, one can replenish the reservoir with therapeutic medium to compensate for the depletion of the therapeutic medium as it is being instilled subretinally. Also, a physician can alter or modify or adjust the therapeutic medium to be instilled also though such injecting.

According to another aspect of the present invention, there are featured methods using such a therapeutic delivery device for each of the desired presentations. Typically, the therapeutic medium delivery devices is implantated in the eye/body of the patient under local anesthesia in the operating room, with or without the need of vitrectomy. For an a therapeutic delivery device that is disposed external, the reservoir portion is fixed on the pars plana, when necessary digitally the drug may be released. The pars plana reservoir is introduced through a sclerotomy and implanted within the posterior chamber of the eye. In an exemplary embodiment, a ring-like reservoir is incorporated to the periphery of an intraocular lens, and the lens is placed either to the anterior or posterior chamber. In order to fix the therapeutic medium delivery device so as to stay on the retina, a tack may be introduced through a tack hole on the reservoir and insetted into the retina-choroid-sclera.

After the reservoir of the therapeutic medium delivery device is localized to a given location associated with the a particular presentation, the cannula emerging from the reservoir is routed/manipulated so as travel inside the vitreous and is inserted into the retina. In more specific embodiments, the cannula is secured subretinally with or without a retinal tack.

As indicated above, in another embodiment after the release of the therapeutic medium (in particular proteins) inside the reservoir, the reservoir can be re-loaded or re-filled with additional therapeutic medium as well as adjusting the strength and constitution of the therapeutic medium to be administered. Such re-filling or reloading is accomplished, for example, under topical anesthesia, under sterile conditions, using, for example, a needle with a syringe loaded with the drug/therapeutic, piercing the polymer of the reservoir, which can withstand many injections without any leakage. This procedure can be repeated using indirect ophthalmoscopy and loupe or under the operating microscope. After the treatment of the disease, according to the conditions, the therapeutic medium delivery device of the present invention can be kept in place or it can be removed.

As indicated above, in particular embodiments, the therapeutic medium delivery device is configured and arranged so as to disperse the therapeutic medium subretinally physiologically via the retinal pigment epithelium pump. This shall not be construed as being limiting as it is contemplated that the therapeutic delivery device also can be configured so as to be capable of being pumped using any of a number of other means known to those skilled in the art by which therapeutic medium within the reservoir can be dispensed from the cannula. For example, a force can be applied to the exterior of an externally located reservoir thereby causing therapeutic medium to flow from the reservoir. This force could be generated, for example, by having a finger of the physician or patient pushing against the reservoir.

Most, if not all, ophthalmic diseases and disorders are associated with one or more of three types of indications: (1) angiogenesis, (2) inflammation, and (3) degeneration. Based on the indications of a particular disorder, one of ordinary skill in the art can administer any suitable therapeutic medium molecule from the three groups at a therapeutic dosage. The following describes some ophthalmic diseases and disorders and a form of treatment therefore. It should be recognized however, that the following is by way of illustration and is not intended to limit the methodologies of the present invention to a particular technique or therapeutic medium for treatment of an eye disease or disorder.

Diabetic retinopathy, for example, is characterized by angiogenesis. This invention contemplates treating diabetic retinopathy by delivering one or more anti-angiogenic factors into the sub-retinal space. It also is desirable to co-deliver one or more neurotrophic factors also to the sub-retinal space.

Uveitis involves inflammation. The present invention contemplates treating uveitis by instilling or disposing one or more anti-inflammatory factors in the sub-retinal space.

Retinitis pigmentosa, by comparison, is characterized by retinal degeneration. The present invention contemplates treating retinitis pigmentosa-by instilling or disposing one or more neurotrophic factors in the sub-retinal space.

Age-related macular degeneration involves both angiogenesis and retinal degeneration and includes, but is not limited to, dry age-related macular degeneration, exudative age-related macular degeneration, and myopic degeneration. The present invention contemplates treating this disorder by instilling or disposing in the sub-retinal space one or more neurotrophic factors and/or one or more anti-angiogenic.

More particularly, the methodology contemplates instilling or disposing a corticosteriod in the sub-retinal space.

Glaucoma is characterized by increased ocular pressure and loss of retinal ganglion cells. Treatments for glaucoma contemplated in the present invention include delivery of one or more neuroprotective agents that protect cells from excitotoxic damage. Such agents include N-methyl-D-aspartate (NMDA) antagonists, cytokines, and neurotrophic factors.

Other aspects, embodiments and advantages of the present invention will become readily apparent to those skilled in the art are discussed below. As will be realized, the present invention is capable of other and different embodiments without departing from the present invention. Thus the following description as well as any drawings appended hereto shall be regarded as being illustrative in nature and not restrictive.

DEFINITIONS

The instant invention is most clearly understood with reference to the following definitions:

Vitreous shall be understood to mean the vitreous or vitreal cavity of a mammalian eye.

Aqueous of the eye shall be understood to mean the aqueous humor of the eye.

As used herein, "therapeutically effective amount" refers to that amount of a therapeutic medium alone, or together with other substances, that produces the desired effect (such as treatment of a medical condition such as a disease or the like, or alleviation of pain) in a patient. During treatment, such amounts will depend upon such factors as the particular condition being treated, the severity of the condition, the individual patient parameters including age, physical condition, size and weight, the duration of the treatment, the nature of the particular bioactive agent thereof employed and the concurrent therapy (if any), and like factors within the knowledge and expertise of the health practitioner. A physician or veterinarian of ordinary skill can readily determine and prescribe the effective amount of the therapeutic medium required to treat and/or prevent the progress of the condition.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DESCRIPTION OF THE PREFERRED EMBODIMENT

Figure 1A:
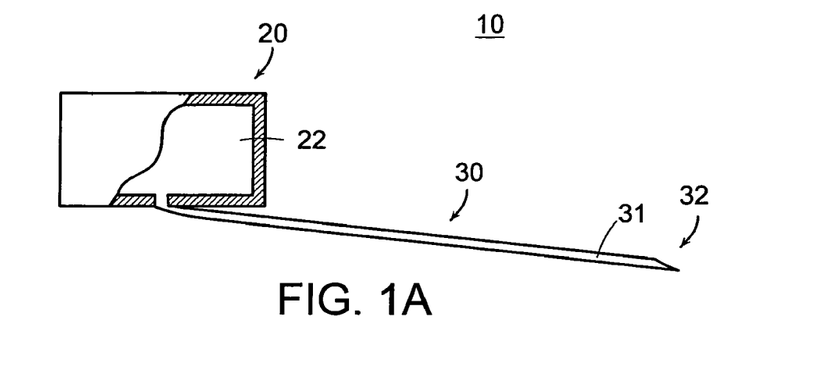
FIG. 1A is a block diagram view illustrating a therapeutic medium drug delivery device according to the present invention.

Referring now to the various figures of the drawing wherein like reference characters refer to like parts, there is shown in FIG. 1A a simplified block diagram or schematic view of a therapeutic medium delivery device 10 according to the present invention. As shown in FIG. 1A, the therapeutic medium delivery device 10 includes a main body 20 and a outlet member or cannula 30 that is fluidly coupled to the interior volume 22 or compartment of the main body. The cannula 30 also is arranged so as to extend outwardly from the main body and from any one of the bottom, side or top surfaces of the main body.

The main body 20, more specifically the main body interior volume, is sized so as to contain a desired amount of the therapeutic medium to be dispensed or instilled subretinally in the eye 2. In the case where the therapeutic delivery device 10 is disposed within the eye 2, the main body 20 also is preferably sized so as to not cause an appreciable impact on the vision of a patient when it is located in the eye.

Figure 1B:
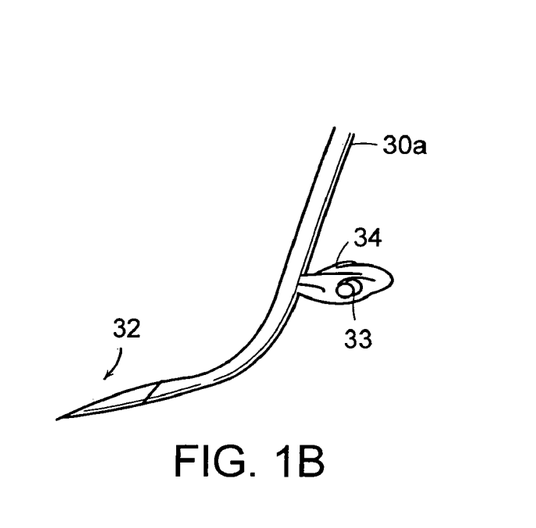
FIG. 1B is an illustrative view of an end of a cannula according to an embodiment of the present invention configured so the end is secured to the retina by a tack.
Figure 1C:
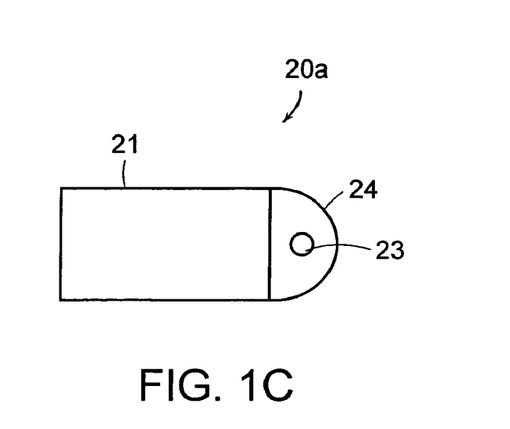
FIG. 1C is an illustrative view of a side of a reservoir member according to an embodiment of the present invention configured so as to be secured to the retina by a tack.

In more particular embodiments, and with reference also to FIG. 1C, the main body 20a is configurable so as to be secured to interior surfaces of the eye, when the therapeutic medium delivery device is disposed within the eye 2. In the illustrated embodiment, the main body 20a includes a body portion 21 and a tab member 24. The body portion 21 is generally configured so as to include the main body interior volume 22 and the tab member 24 includes a through aperture 23. The through aperture 23 is sized so as to receive therein the securing mechanism or device that secures the main body to interior portions or features of the eye. In an illustrative embodiment, and as discussed further herein the tab member is secured to the retina 4.

The cannula 30 includes an axially extending passage or lumen 31 that extends from the point of fluid coupling of the main body interior volume 22 to the end 32 of the cannula. The therapeutic medium in the interior volume 22 flows through the lumen 31 to the end of the cannula. The end 32 of the cannula 30 is configured and arranged using any of a number of techniques known to those skilled in the art so as to control the release of the therapeutic medium after the end is disposed sub-retinally. In particular embodiments, the cannula end 32 is configured and arranged so that the therapeutic medium flows from the lumen into the subretinal region responsive physiologically via the retinal pigment epithelium pump.

In further embodiments, the cannula end 30 is configured and arranged so as to facilitate the insertion of the cannula end through the retina 4 and so that the end and certain portions of the cannula are located sub-retinally as more particularly illustrated in FIGS. 2-5 that follow. In a particular embodiment, the cannula end 32 includes a sloped surface having a generally pointed tip so as to facilitate such insertion through the retina 2 and so as to be disposed in a region between the retina and chorid of the eye.

The length of the cannula 30 is established based on the particular application so the cannula end 32 and portions of the cannula proximal to the end 32 can be disposed proximal the treatment site, and so the main body 20 can be positioned in any of a number of other locations or positions as more particularly described hereinafter in regards to FIGS. 2-5. The cannula 30 also is sized (e.g., cross-section) so the lumen 31 therein forms an effective transport path for transport the therapeutic medium from the interior volume 22 to the cannula end 32 and so the cannula does not unduly restrict (e.g., occlude) the vision of the patient. In more specific embodiments, and in the case where the main body is disposed external to the eye, the cannula 30 is sized such that when the cannula 30 is removed from the eye the through aperture is self-sealing and thus does not require suturing of the opening in the eye.

As indicated above, the main body interior volume 22 is filled with a therapeutic medium and thus forms a reservoir of the therapeutic medium. In this way, the therapeutic delivery device of the present invention provides a mechanism for sub-retinal administration or delivery of a therapeutic medium to a posterior segment of a mammalian eye, more particularly a human eye as well as a methodology for treating and/or preventing disorders and/or diseases of the eye, in particular retinal/choroidal disorders or diseases, through such sub-retinal administration of such therapeutic mediums. Such methodologies provide a mechanism for treating a wide array of diseases and/or disorders of an eye of a mammal, more specifically a human eye, and more particularly diseases or disorders involving the posterior segment of the eye such as retinal/choroidal disorders or diseases. Such a treatment/prevention methodology also is useable to treat/prevent a number of vision-threatening disorders or diseases of the eye of a mammal including, but not limited to diseases of the retina, retinal pigment epithelium (RPE) and choroid. Such vision threatening diseases include, for example, ocular neovascularization, ocular inflammation and retinal degenerations. Specific examples of these disease states include diabetic retinopathy, chronic glaucoma, retinal detachment, sickle cell retinopathy, age-related macular degeneration, retinal neovascularization, subretinal neovascularization; rubeosis iritis inflammatory diseases, chronic posterior and pan uveitis, neoplasms, retinoblastoma, pseudoglioma, neovascular glaucoma; neovascularization resulting following a combined vitrectomy and lensectomy, vascular diseases retinal ischemia, choroidal vascular insufficiency, choroidal thrombosis, neovascularization of the optic nerve, diabetic macular edema, cystoid macular edema, macular edema, retinitis pigmentosa, retinal vein occlusion, proliferative vitreoretinopathy, angioid streak, and retinal artery occlusion, and, neovascularization due to penetration of the eye or ocular injury. The methodology of the present invention also can be used to treat ocular symptoms resulting from diseases or conditions that have both ocular and non-ocular symptoms. Such a therapeutic medium delivery device 10 according to the present invention, as well as related methods, bypass the mechanisms or barriers that limit effective delivery of such therapeutic mediums if injected directly into the vitreous, thereby permitting more sustained therapy for the target tissue(s). Moreover, because such a delivery device 10 locates the therapeutic medium sub-retinally (e.g., in the sub-retinal space) the side effects typically associated with the injection of drugs into the vitreous (e.g., elevated intraocular pressure) are reduced. Because the deliver device 10 administers the therapeutic medium sub-retinally, this also minimizes the loss or removal of the therapeutic medium from the eye such as expiration of the therapeutic medium via the anterior segment of the eye after being initially located or injected in the vitreous. Also, such sub-retinal locating of the therapeutic medium minimizes the need for follow up injections, as typically needed with injections into the vitreous in order to maintain an adequate therapeutic concentration within the vitreous as well as minimizing the risks attendant with such injections to the vitreous. Further, because the therapeutic medium is delivered directly to the subretinal space, it follows that higher concentrations of the medium are delivered to the choroidal vessels and retinal pigment epithelial cells as compared to intravitreal injection and intraocular implants that introduce drugs into the vitreous humor.

As used in the present invention, therapeutic medium includes any compound, agent or the like known in the art that when administered or delivered sub-retinally, is effective in obtaining a desired local or systemic physiological or pharamacological effect. More particularly, in the present invention, therapeutic medium includes, but is not limited to drugs, medicaments, antibiotics, antibacterials, antiproliferatives, neuroprotectives, anti-inflammatories (steroidal and non-sterodial), growth factors, neurotropic factors, antiangiogenics, thrombolytics or genes. Exemplary therapeutic mediums include, but are not limited to, thrombin inhibitors; anti-thrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1-3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Antiproliferatives include any of a number of compounds, agents, therapeutic mediums or drugs known to those skilled in the art that inhibit the proliferation of cells. Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized has having the property of counteracting or suppressing the inflammatory process. Non-steroidal inflammatory drugs or compounds comprise a class of drugs which shares the property of being analgesic, antipyretic and anti-inflammatory by way of interfering with the synthesis of prostaglandins. Such non-steroidal anti-inflammatories include, but are not limited to, indomethacin, ibuprofen, naxopren, piroxicam and nabumetone.

Such anti-inflammatory steroids contemplated for use in the methodology of the present invention, include those described in U.S. Pat. No. 5,770,589, the teachings of which are incorporated herein by reference. In an exemplary embodiment, an anti-inflammatory steroid contemplated for use in the methodology of the present invention is triamcinolone acetonide (generic name). Corticosteroids contemplated for use in the methodology of the present invention include, for example, triamcinolone, dexamethasone, fluocinolone, cortisone, prednisolone, flumetholone, and derivatives thereof (See also U.S. Pat. No. 5,770,589).

Other anti-inflammatories or anti-inflammatory factors contemplated for use in the present invention include anti-flammins (see, e.g. U.S. Pat. No. 5,266,562, incorporated herein by reference in its entirety), beta-interferon (IFN-.beta.), alpha-interferon (IFN-.alpha.), TGF-beta, interleukin-10 (XL-10), and glucocorticoids and mineralocorticoids from adrenal cortical cells. It should be noted that certain biologically active materials can have more than one activity. For example, it is believed that IFN-.alpha. and IFN-.beta. have activities as both anti-inflammatory molecules and as anti-angiogenic molecules. In exemplary embodiments, the dosage of anti-inflammatory factors being delivered to the sub-retinal space is contemplated as being in a dosage range of 50 pg to 500 ng, preferably 100 pg to 100 ng, and most preferably 1 ng to 50 ng per eye per patient per day.

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation. In the present invention, such growth factors include, but are not limited to, pigment epithelium derived factor and basic fibroblast growth factor.

As is known to those skilled in the art, neurotropic factors is a general term used to describe growth factors and cytokines that can enhance neuronal survival and axonal growth and that regulate synaptic development and plasticity in the nervous system. In the present invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries. Such compounds, agents, therapeutic mediums or drugs include, but are not limited to, anecortave acetate and anti VEGF antibody. Other antiangiogentics or anti-angiogenic factors contemplated for use with the methodology of the present invention include vasculostatin, angiostatin, endostatin, anti-integrins, vascular endothelial growth factor inhibitors (VEGF-inhibitors), platelet factor 4, heparinase, and bFGF-binding molecules. The VEGF receptors Flt and Flk are also contemplated. When delivered in the soluble form these molecules compete with the VEGF receptors on vascular endothelial cells to inhibit endothelial cell growth. VEGF inhibitors may include VEGF-neutralizing chimeric proteins such as soluble VEGF receptors. See Aiello, PNAS, 92, 10457 (1995). In particular, they may be VEGF-receptor-IgG chimeric proteins. Another VEGF inhibitor contemplated for use in the present invention is antisense phosphorothiotac oligodeoxynucleotides (PS-ODNs). In exemplary embodiments, the dosage of anti-angiogenic factors being delivered to the sub-retinal space is contemplated as being in a dosage range of 50 pg to 500 ng, preferably 100 pg to 100 ng, and most preferably 1 ng to 50 ng per eye per patient per day.

Thrombolytics, as is known to those skilled in the art include any of a number of compounds, agents, therapeutic mediums or drugs that dissolve blot clots, or dissolve or split up a thrombous. Such thrombolytics include, but are not limited to, streptokinase, tissue plasminogen activator or TPA and urokinase.

Other factors contemplated for use in the present invention for retarding cell degeneration, promoting cell sparing, or promoting new cell growth include neurotrophin 4/5 (NT4/5), cardiotrophin-1 (CT-1), ciliary neurotrophic-factor (CNTF), glial cell line derived neurotrophic factor (GDNF), nerve growth factor (NGF), insulin-like growth factor-1 (IGF-1), neurotrophin 3 (NT-3), brain-derived neurotrophic factor (BDNF), PDGF, neurturin, acidic fibroblast growth factor (aFGF), basic fibroblast growth factor (bFGF), EGF, neuregulins, heregulins, TGF-alpha, bone morphogenic proteins (BMP-1, BMP-2, BMP-7, etc.), the hedgehog family (sonic hedgehog, Indian hedgehog, and desert hedgehog, etc.), the family of transforming growth factors (including, e.g., TGF.beta.-1, TGF.beta.-2, and TGF.beta.-3), interleukin 1-B (IL1-.beta.), and such cytokines as interleukin-6 (EL-6), IL-10, CDF/LIF, and beta-interferon (IFN-.beta.). In exemplary embodiments, the dosage of such factors being delivered to the sub-retinal space is contemplated as being in a dosage range of 50 pg to 500 ng, preferably 100 pg to 100 ng, and most preferably 1 ng to 50 ng per eye per patient per day.

Modified, truncated, and mutein forms of the above-mentioned molecules are also contemplated. Further, active fragments of these growth factors (i.e., those fragments of growth factors having biological activity sufficient to achieve a therapeutic effect) are also contemplated; Also contemplated are growth factor molecules modified by attachment of one or more polyethylene glycol (PEG) or other repeating polymeric moieties. Combinations of these proteins and polycistronic versions thereof are also contemplated.

The therapeutic medium delivery device 10 and methodology of the present invention advantageously delivers the therapeutic medium to the target or disease site and thus the eye as compared to current systemic and intraocular routes of administration. More particularly, the delivery device 10 and methodology of the present invention allows the highest achievable drug concentration at the target or disease site, a low dosage requirement, and minimal aqueous and vitreous concentrations, thereby consequently reducing side effects (e.g., glaucoma, cataract, etc.) that can be exhibited when using current techniques.

It is understood that the amount of the therapeutic medium that is to be delivered to the treatment site is readily calculable by one of ordinary skill in the art without undue experimentation and will vary depending on the disease or disorder to be treated and the particular treatment circumstances. In addition, the amount also will depend upon the particular formulation of the therapeutic medium. Further, the amount of the therapeutic medium to be delivered also takes into account the period of time expected for administration and/or treatment and/or the frequency or periodicity of such administration and/or treatment. The formulation also ordinarily takes into account pH, osmolarity and toxicity. In more particular embodiments, the therapeutic medium is in the form of one of a solution, a composition or a liquid.

The therapeutic medium also can include a pharmaceutically acceptable carrier or excipient and/or one or more accessory molecules which may be suitable for diagnostic or therapeutic use in vitro or in vivo. The term "pharmaceutically acceptable carrier" as used herein encompasses any of the standard pharmaceutical carriers, such as a phosphate buffered saline solution, water, and emulsions, such as an oil/water or water/oil emulsion, and various types of wetting agents. The therapeutic medium also can include stabilizers and preservatives. For examples of carriers, stabilizers and adjuvants, see Martin *Remington's Pharm. Sci.,* 15th Ed. (Mack Publ. Co., Easton (1975)).

It also should be recognized, that the therapeutic medium delivery device 10 and methodologies of the present invention are contemplated as being practiced alone, or in combination with other therapies or treatments. For example, where laser treatment of an eye is indicated, the, therapeutic medium delivery device 10 can be used so the cannula end 32 is positioned subretinally so the delivery device can administer therapeutics sub-retinally before and/or after the laser treatment. In addition, it is contemplated that the therapeutic medium can comprise a mixture of active agents or therapeutic agents such as for example antibiotics, medicaments, or agents, e.g., thalidomide, being administered along with a steroid.

Most, if not all, ophthalmic diseases and disorders are associated with one or more of three types of indications: (1) angiogenesis, (2) inflammation, and (3) degeneration. Based on the indications of a particular disorder, one of ordinary skill in the art can administer any suitable therapeutic medium molecule from the three groups at a therapeutic dosage. The following describes some ophthalmic diseases and disorders and a form of treatment therefore. It should be recognized however, that the following is by way of illustration and is not intended to limit usage of the therapeutic medium delivery device or methodologies of the present invention to a particular technique or therapeutic medium for treatment of an eye disease or disorder.

Diabetic retinopathy for example, is characterized by angiogenesis. This invention contemplates treating diabetic retinopathy by delivering one or more anti-angiogenic factors into the sub-retinal space. It also is desirable to co-deliver one or more neurotrophic factors also to the sub-retinal space.

Uveitis involves inflammation. The present invention contemplates treating uveitis by instilling or disposing one or more anti-inflammatory factors in the sub-retinal space.

Retinitis pigmentosa, by comparison, is characterized by retinal degeneration. The present invention contemplates treating retinitis pigmentosa by instilling or disposing one or more neurotrophic factors in the sub-retinal space.

Age-related macular degeneration involves both angiogenesis and retinal degeneration and includes, but is not limited to, dry age-related macular degeneration, exudative age-related macular degeneration, and myopic degeneration. The present invention contemplates treating this disorder by instilling or disposing in the sub-retinal space one or more neurotrophic factors and/or one or more anti-angiogenic. More particularly, the methodology contemplates instilling or disposing a corticosteriod in the sub-retinal space.

Glaucoma is characterized by increased ocular pressure and loss of retinal ganglion cells. Treatments for glaucoma contemplated in the present invention include delivery of one or more neuroprotective agents that protect cells from excitotoxic damage. Such agents include N-methyl-D-aspartate (NMDA) antagonists, cytokines, and neurotrophic factors.

As noted above, administration of the therapeutic medium is not limited to those uses involving the diagnosed existence of a disorder or disease. It is contemplated that the therapeutic medium; delivery device can be used for prophylactic administration of the therapeutic medium. For example, in more than 50% of cases where AMD occurs in one eye, it will subsequently occur in the unaffected eye within a year. In such cases, prophylactic administration of a therapeutic medium such as a steroid into the unaffected eye may prove to be useful in minimizing the risk of, or preventing, AMI in the unaffected eye.

In FIG. 1B there is shown a further embodiment of a cannula 30a according to the present invention. Reference shall be made to the foregoing discussion regarding FIG. 1A as to other details, features and characteristics of the cannula 30a not otherwise provided below. In the illustrated embodiment, the cannula 30a further includes a tab member 34 that is located proximal the cannula end 32, which tab member is configurable so as to be secured to interior surfaces of the eye, thereby providing a further mechanism for securing the cannula end 32 so that it remains disposed subretinally. In particular embodiments, the cannula tab member 34 includes a through aperture 33 that is sized so as to receive therein the securing mechanism or device that secures the cannula tab member to interior portions or features of the eye. In an illustrative embodiment, and as discussed further herein the cannula tab member 34 is secured to the retina 4.

Referring now to FIGS. 2-5 there are shown various views illustrating the use of and various configurations of a therapeutic medium delivery device according to the present invention. Reference shall be made to the foregoing discussion regarding the main body 20,20a and cannula 30,30a illustrated in FIGS. 1A-C for further details, features and characteristics of the main body and cannula of FIGS. 2-5 except as otherwise described below.

Figure 2:
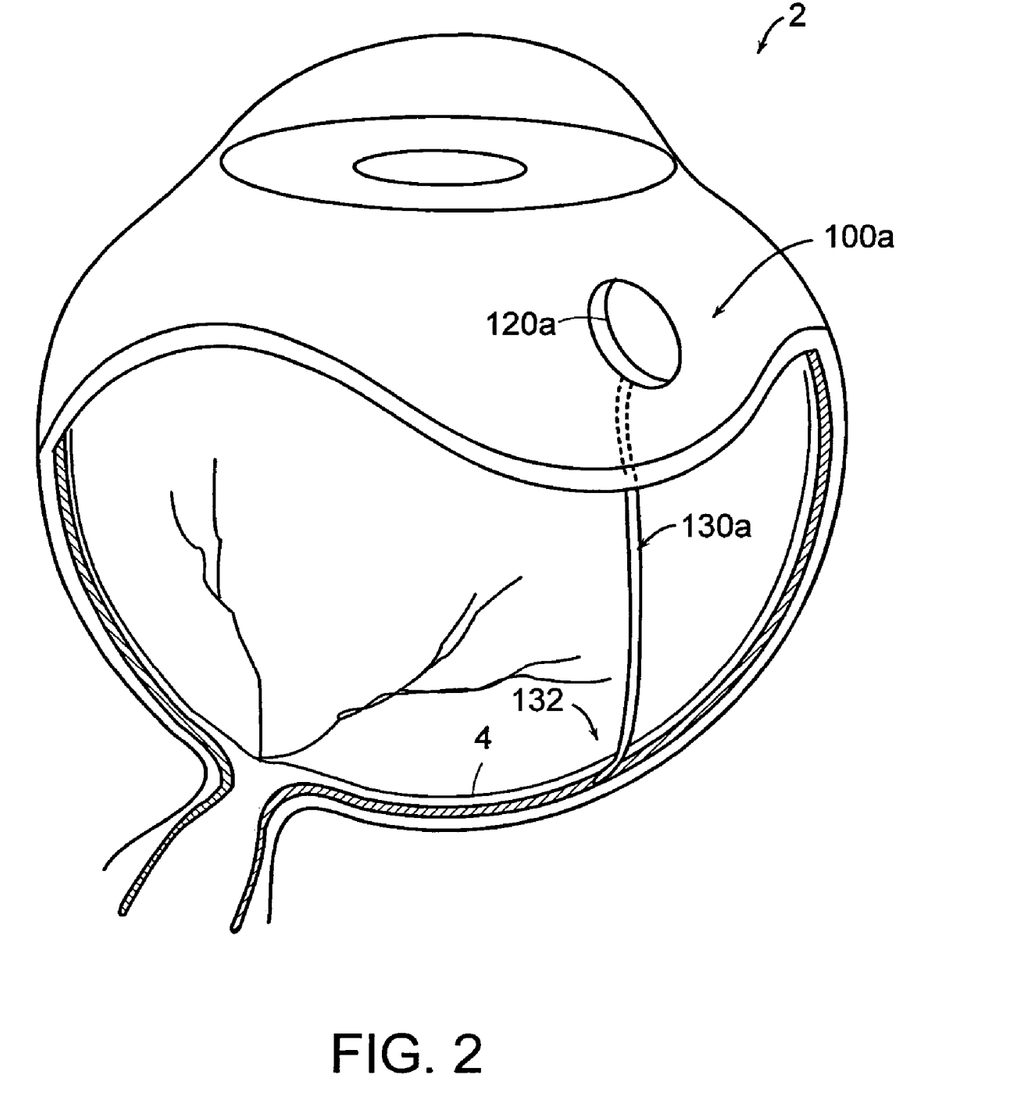
FIG. 2 is an illustrative view of an eye illustrating the external reservoir presentation.

Referring now to FIG. 2, there is shown a therapeutic medium delivery device 100a in which the main body 120a thereof is arranged so as to be external to the posterior of the eye 2. More particularly, the main body 120a is arranged so as to be disposed generally upon the sclera of the eye, more specifically disposed on the pas plana. In more particular embodiments, the externally located main body 120a is secured to the pars plana or sclera using any of a number of techniques known to those in the art such as, but not limited to sutures and staples. The main body 120a in such an arrangement forms an external reservoir.

The cannula 130a is inserted through the sclera of the eye 2 using any of a number of techniques known to those skilled in the art (e.g., a sclerotomy), so the end 132 thereof is located in the vitreous. Thereafter, and using any of a number of techniques known to those in the art, the cannula 130a including the cannula end 132 is manipulated within the vitreous and so the cannula end 132 is inserted through the retina 4 so as to be proximal the treatment site. The cannula end 132 is preferably inserted subretinally a sufficient amount to ensure release of the therapeutic medium subretinally and so the cannula end 132 is retained subretinally. It is within the scope of the present invention for the cannula end 132 to be secured in place such as that illustrated in FIGS. 3A,B.

Thereafter the therapeutic medium within the main body 120a is released into the subretinal space and thus to the tissues proximal the treatment site. As indicated herein, the main body interior volume 22 (FIG. 1A) can be reloaded as the need arises with additional therapeutic medium. Following a course of treatment, and according to the other medical considerations, the therapeutic medium deliver device 100a is either removed using appropriate surgical techniques or the deliver device 100a is kept in place, such as for possible future use.

Figure 3A:
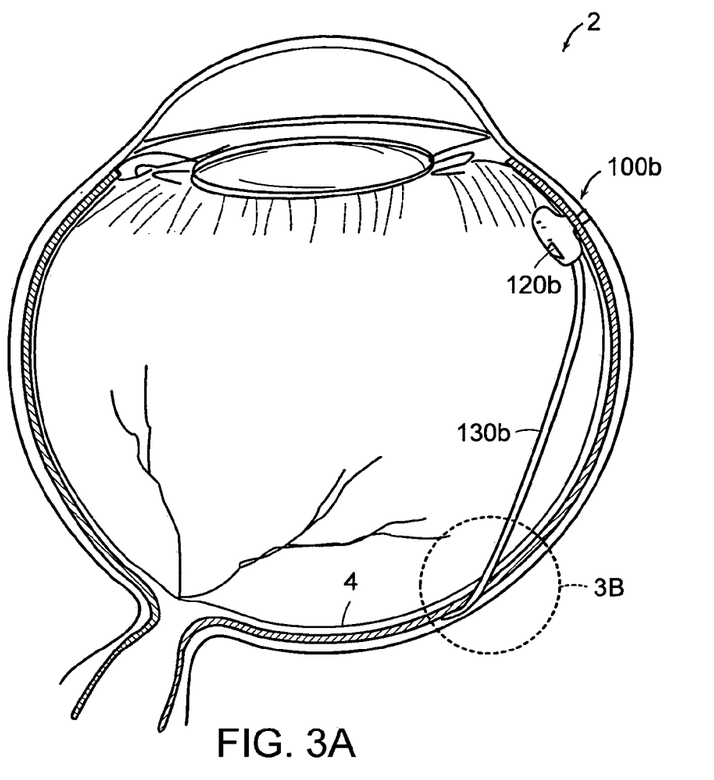
FIG. 3A is an illustrative view of an eye illustrating the pars plana reservoir presentation.
Figure 3B:
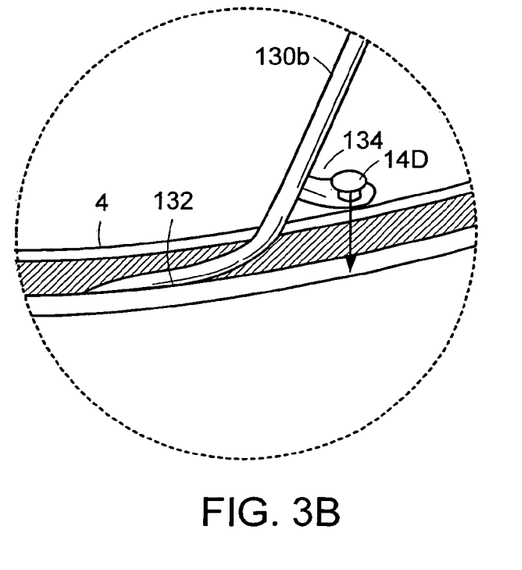
FIG. 3B is an enlarged partial view of the ballooned area of FIG. 3A.

Referring now to FIG. 3A, there is shown a therapeutic medium delivery device 100b in which the main body 120b thereof is arranged so as to be internal to the posterior of the eye 2 or within the vitreous. More particularly, the main body 120b is introduced via a sclerotomy and implanted upon the pars plana. In more particular embodiments, the main body 120a is secured to the pars plana using any of a number of techniques known to those in the art such as, but not limited to sutures and staples. The main body 120a in such an arrangement forms a pars plana reservoir.

Using any of a number of techniques known to those in the art, the cannula 130a including the cannula end 132 is manipulated within the vitreous and so the cannula end 132 is inserted through the retina 4 so as to be proximal the treatment site. The cannula end 132 is preferably inserted subretinally a sufficient amount to ensure release of the therapeutic medium subretinally and so the cannula end 132 is retained subretinally. In further embodiments, the cannula end 132 is secured in place by means of a retinal tack 140, as is known in the art, that passes through the tab member through aperture 134 as is illustrated in FIG. 3B. In specific embodiments, the retinal tack is inserted through the retina-choroid-sclera.

Thereafter, the therapeutic medium within the main body 120b is released into the subretinal space and thus to the tissues proximal the treatment site. As indicated herein, the main body interior volume 22 (FIG. 1A) can be reloaded as the need arises with additional therapeutic medium. Following a course of treatment, and according to the other medical considerations, the therapeutic medium deliver device 100b is either removed using appropriate surgical techniques or the deliver device 100b is kept in place, such as for possible future use.

Figure 4:
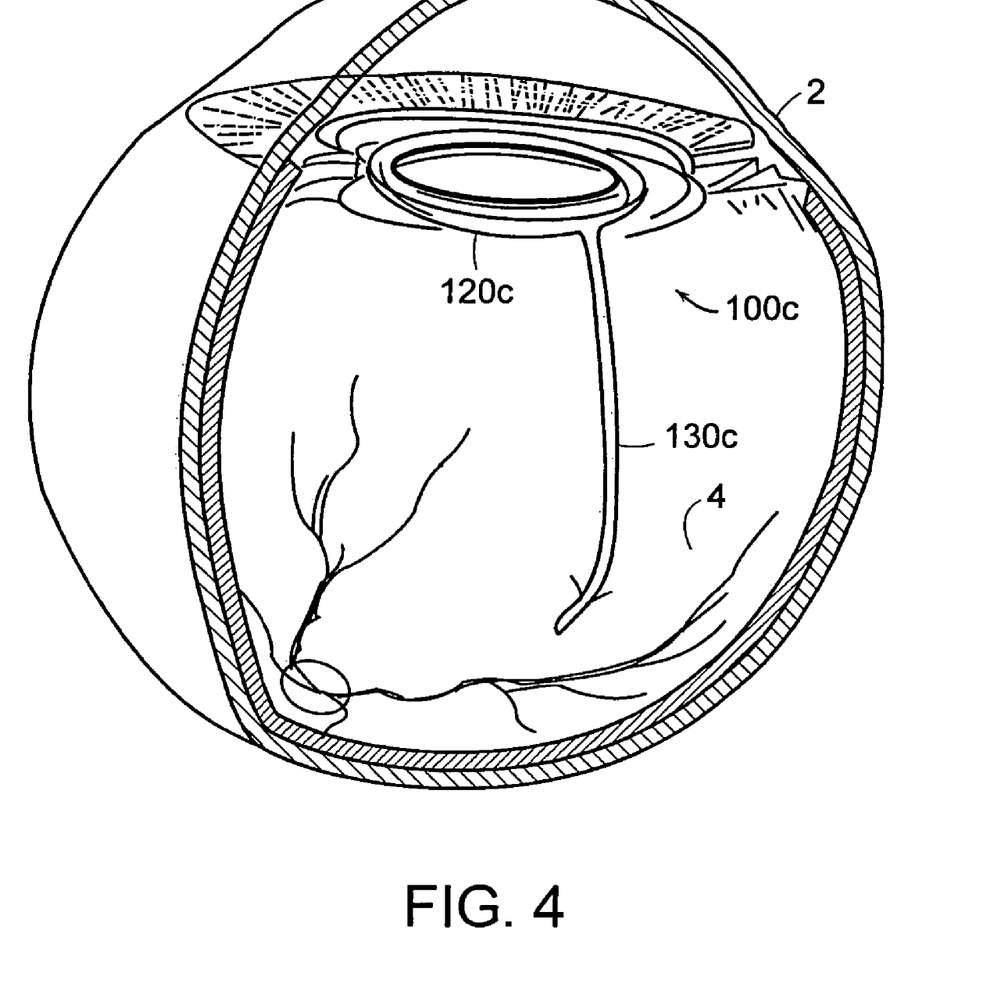
FIG. 4 is an illustrative view of an eye illustrating the intraocular lens reservoir presentation.

Referring now to FIG. 4, there is shown a therapeutic medium delivery device 100c in which the main body 120c thereof is configured and arranged so as to form a ring like structure that can be incorporated to the periphery of an intraocular lens and thus is placed in either the anterior chamber or posterior chamber of the eye. The ring-like structure comprising the main body 120c would be inserted along with the lens. The main body 120c in such an arrangement forms an intraocular lens reservoir.

Using any of a number of techniques known to those in the art, the cannula 130c including the cannula end 132 is manipulated within the vitreous and so the cannula end 132 is inserted through the retina 4 so as to be proximal the treatment site. The cannula end 132 is preferably inserted subretinally a sufficient amount to ensure release of the therapeutic medium subretinally and so the cannula end 132 is retained subretinally. In further embodiments, the cannula end 132 is secured in place by means of a retinal tack 140, as is known in the art, that passes through the tab member through aperture 134 as is illustrated in FIG. 3B.

Thereafter, the therapeutic medium within the main body 120c is released into the subretinal space and thus to the tissues proximal the treatment site. As indicated herein, the main body interior volume 22 (FIG. 1A) can be reloaded as the need arises with additional therapeutic medium. Following a course of treatment, and according to the other medical considerations, the therapeutic medium deliver device 100c is either removed using appropriate surgical techniques or the deliver device 100c is kept in place, such as for possible future use.

Figure 5:
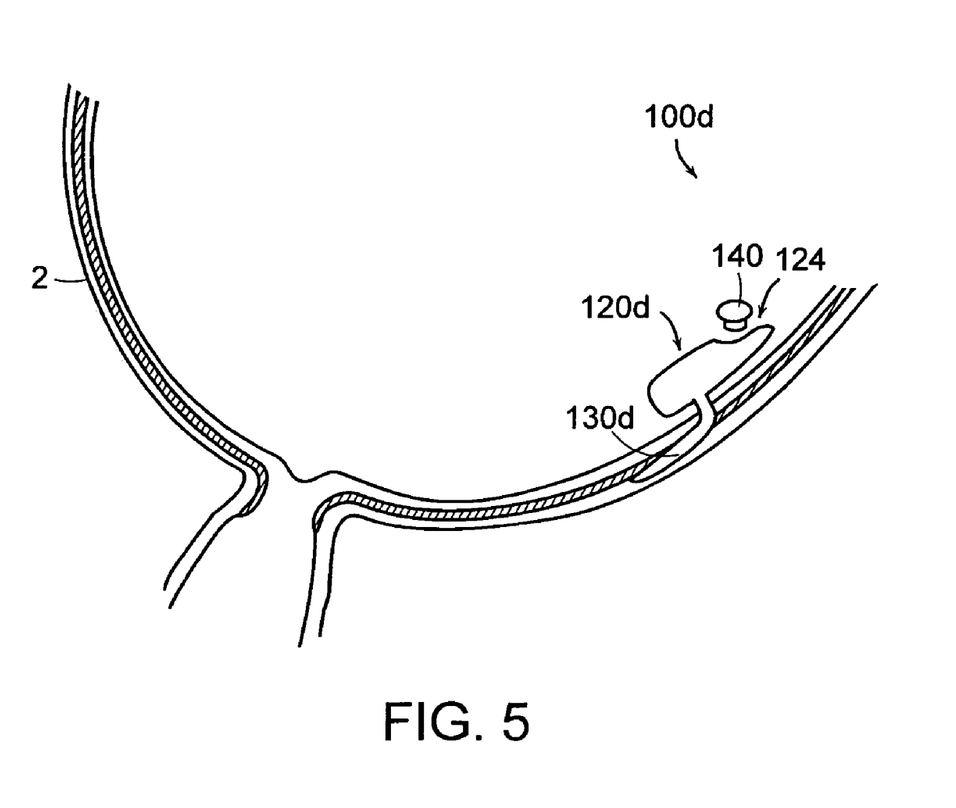
FIG. 5 is an illustrative cross-sectional view of a portion of eye illustrating the epiretinal reservoir presentation.

Referring now to FIG. 5, there is shown a therapeutic medium delivery device 100d in which the main body 120d thereof is arranged so as to be internal to the posterior of the eye 2 or within the vitreous. More particularly, the main body 120d is introduced via a sclerotomy and implanted upon the retina. In more particular embodiments, the main body 120a is secured to the retina using any of a number of techniques known to those in the art. In further embodiments, the main body 120d is secured in place by means of a retinal tack 140, as is known in the art, that passes through the tab member through aperture 123 (FIG. 1C), and in more specific embodiments the retinal tack is inserted through the retina-choroid-sclera. The main body 120a in such an arrangement forms a epiretinal reservoir.

Using any of a number of techniques known to those in the art, the cannula 130d including the cannula end 132 is manipulated within the vitreous and so the cannula end 132 is inserted through the retina 4 so as to be proximal the treatment site. The cannula end 132 is preferably inserted subretinally a sufficient amount to ensure release of the therapeutic medium subretinally and so the cannula end 132 is retained subretinally. In further embodiments, the cannula end, 132 can be secured/further secured in place by means of a retinal tack 140 that passes through the tab member through aperture 134 as is illustrated in FIG. 3B.

Thereafter, the therapeutic medium within the main body 120d is released into the subretinal space and thus to the tissues proximal the treatment site. As indicated herein, the main body interior volume 22 (FIG. 1A) can be reloaded as the need arises with additional therapeutic medium. Following a course of treatment, and according to the other medical considerations, the therapeutic medium deliver device 100d is either removed using appropriate surgical techniques or the deliver device 100d is kept in place, such as for possible future use.

Although a preferred embodiment of the invention has been described using specific terms, such description is for illustrative purposes only, and it is to be understood that changes and variations may be made without departing from the spirit or scope of the following claims.

Incorporation by Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A subretinal delivery device comprising:
    a reservoir;
    a cannula extending from the reservoir, the cannula having a length and being configured such that it extends from the reservoir through the vitreous and through the retina with a distal end terminating in a subretinal space when the reservoir is disposed exterior the eye on the sclera or when the reservoir is disposed within the eye;
    a securing mechanism near the distal end of the cannula configured to secure a distal portion of the cannula to the retina; and
    wherein the cannula is configured so that an agent in the reservoir is released from the reservoir through the cannula to the eye subretinally.

2. The device of claim 1, wherein the reservoir is an external reservoir.

3. The device of claim 2, wherein the external reservoir is fixed on the pars plana.

4. The device of claim 1, wherein the reservoir is a pars plana reservoir.

5. The device of claim 4, wherein the pars plana reservoir is introduced through a sclerotomy and implanted within the eye.

6. The device of claim 1, wherein the reservoir is an intraocular lens reservoir.

7. The device of claim 6, wherein the intraocular lens reservoir is incorporated to the periphery of an intraocular lens, and the lens is placed either to the anterior or posterior chamber.

8. The device of claim 7, wherein the reservoir is a ring-like.

9. The device of claim 1, wherein the reservoir is an epiretinal reservoir.

10. The device of claim 9, wherein the epiretinal reservoir is fixed on the retina via a tack through an aperture in the reservoir.

11. The device of claim 9, wherein the cannula emerges from the reservoir, travels inside the vitreous and inserts into the retina.

12. The device of claim 1, wherein the reservoir is fabricated of a polymer.

13. The device of claim 1, wherein the cannula end is disposed subretinally so as to release the agent through the subretinal space, physiologically via the retinal pigment epithelium pump.

14. The device of claim 1, wherein the reservoir is configured and arranged so it can be reloaded with agent.

15. The device of claim 14, wherein the reservoir is configured and arranged so such reloading can be accomplished by piercing the reservoir with an injection device and injecting the agent therein without the formation of a leak.

16. The device of claim 15, wherein the injection device is a syringe.

17. The device of claim 1, wherein the reservoir can withstand multiple injections without leakage.

18. The device of claim 1 wherein the securing mechanism is a tab near the distal end of the cannula that is securable to the retina.

19. The device of claim 18 wherein the tab is secured to the retina using a tack.

20. A method for the treatment of ocular conditions comprising the steps of:
    implanting an agent delivery device comprising a reservoir and a cannula extending from the reservoir into the eye such that the reservoir is disposed exterior the eye on the sclera or within the eye, with the cannula extending from the reservoir through the retina into a subretinal space; and
    allowing the agent in the reservoir to be delivered to the eye via the cannula subretinally.

21. The method of claim 20, further comprising the step of: reloading the reservoir with agent.

22. The method of claim 21, wherein said reloading includes piercing the reservoir with an injection device and injecting the agent.

23. The device of claim 22, wherein the injection device is a syringe.

24. The method of claim 20 wherein the agent is controllably delivered to the eye.

25. The method of claim 24 wherein the agent is controllably delivered based at least in part on the cannula design.

26. The method of claim 24 or 25 wherein the agent is controllably delivered at least in part physiologically via the retinal pigment epithelium pump.

27. A subretinal delivery device comprising:
    a reservoir;
    a cannula extending from the reservoir;
    the cannula having a length and being configured to extend from the reservoir through the vitreous and through the retina into a subretinal space when the reservoir is disposed exterior the eye on the sclera or when the reservoir is disposed within the eye;
    the cannula having a pointed distal end for insertion through the retina, the distal end and at least a distal portion of the cannula having a cross-sectional size that allows for disposal and retainment within the subretinal space between the retina and choroid of the eye; and
    wherein an agent in the reservoir is released through the cannula to the eye subretinally.

* * * * *